United States Patent [19]

Cox et al.

[11] Patent Number: 5,430,165

[45] Date of Patent: Jul. 4, 1995

[54] METHOD OF OXIDIZING ALUMINUM ALKYLS

[75] Inventors: William L. Cox; John K. Roberg, both of Houston; Armen N. Abazajian, Friendswood, all of Tex.

[73] Assignee: Albemarle Corporation, Richmond, Va.

[21] Appl. No.: 157,554

[22] Filed: Nov. 26, 1993

Related U.S. Application Data

[60] Continuation-in-part of Ser. No. 47,517, Apr. 19, 1993, Pat. No. 5,278,330, which is a division of Ser. No. 906,199, Jun. 29, 1992, Pat. No. 5,223,103.

[51] Int. Cl.$^6$ .......................... C07F 5/06; C07C 27/00
[52] U.S. Cl. .................................. 556/190; 556/182; 556/185; 568/840; 568/911; 568/922
[58] Field of Search .................. 556/182, 185, 190; 568/911, 922, 840

[56] References Cited

U.S. PATENT DOCUMENTS

| | | | |
|---|---|---|---|
| 2,863,895 | 12/1958 | Kirshenbaum et al. | 260/448 |
| 2,892,858 | 6/1959 | Ziegler | 260/448 |
| 2,921,949 | 1/1960 | Kirshenbaum et al. | 260/448 |
| 2,959,607 | 11/1960 | Werber et al. | 260/448 |
| 3,017,438 | 1/1962 | Atwood | 260/632 |
| 3,042,696 | 7/1962 | Aldridge | 260/448 |
| 3,053,905 | 9/1962 | Coyne et al. | 260/632 |
| 3,087,954 | 4/1963 | McClaflin | 260/448 |
| 3,097,226 | 7/1963 | Napier | 260/448 |
| 3,153,076 | 10/1964 | Wood et al. | 260/448 |
| 3,270,065 | 8/1966 | Austin | 260/632 |
| 3,278,262 | 10/1966 | Poe et al. | 23/143 |
| 3,322,806 | 5/1967 | Asinger et al. | 260/448 |
| 3,389,161 | 6/1968 | Kottong et al. | 260/448 |
| 3,391,175 | 7/1968 | Davis | 260/448 |
| 3,391,219 | 7/1968 | Davis et al. | 260/683.15 |
| 3,474,122 | 10/1969 | Ichiki et al. | 260/448 |
| 3,475,476 | 10/1969 | Cragg et al. | 260/448 |
| 3,487,097 | 12/1969 | Davis | 260/448 |
| 3,494,948 | 2/1970 | Ichiki et al. | 260/448 |
| 3,657,301 | 4/1972 | Motz et al. | 260/448 A |
| 3,660,447 | 5/1972 | Cragg et al. | 260/448 |
| 3,784,623 | 1/1974 | Motz | 260/677 R |
| 3,886,264 | 5/1975 | Lindsay et al. | 423/512 |
| 4,032,582 | 6/1977 | Trebillon | 260/632 D |
| 4,038,322 | 7/1977 | Radzitzky et al. | 260/597 R |
| 4,086,267 | 4/1978 | Bartlett et al. | 560/241 |
| 4,131,742 | 12/1978 | Hudson | 560/241 |
| 4,744,974 | 5/1988 | Lewis et al. | 423/625 |
| 4,918,254 | 4/1990 | Diefenbach et al. | 585/328 |
| 5,124,465 | 6/1992 | Allen | 556/190 |
| 5,142,078 | 8/1992 | Sherif et al. | 556/181 |

FOREIGN PATENT DOCUMENTS 1260864  5/1960  France .

*Primary Examiner*—Porfirio Nazario-Gonzalez
*Attorney, Agent, or Firm*—David M. Bunnell

[57] ABSTRACT

Aluminum alkyls are oxidized to aluminum alkoxides using a cobalt catalyst to increase the rate of oxidation. Alcohols can be prepared by hydrolysis of the aluminum alkoxides.

16 Claims, No Drawings

METHOD OF OXIDIZING ALUMINUM ALKYLS

The application is a continuation-in-part of application Ser. No. 08/047,517, filed Apr. 19, 1993 now U.S. Pat. No. 5,278,330 which is a Divisional of application Ser. No. 07/906,199, filed Jun. 29, 1992, now U.S. Pat. No. 5,223,103, issued Aug. 3, 1993.

Long chain, linear primary alcohols can be prepared by the oxidation and hydrolysis of aluminum alkyls in which one or more, and preferably, all of the alkyl groups contain 12 or more carbon atoms and, more preferably, 14 to 22 carbon atoms. In a typical example of such a process, an aluminum trialkyl intermediate is formed by the chain growth reaction of ethylene with triethylaluminum to produce a mixture of trialkylaluminum compounds having a Poisson distribution of alkyl chain lengths, for example of 2 to 20+ carbon atoms, where the curve peaks at about $C_8$. This aluminum alkyl intermediate is then reacted with a mixture of alpha-olefins having a higher average carbon number than the aluminum alkyl intermediate in order to displace the alkyl groups and form an aluminum alkyl product which has an increased average alkyl chain length. Linear alcohols are then prepared by oxidation and hydrolysis of the aluminum alkyl product.

The oxidation of the aluminum alkyl compounds is usually carried out in two stages. In the first stage molecular oxygen, air, or other molecular oxygen containing material is used to partially (40 to 70%) oxidize the aluminum alkyl to aluminum alkoxides by a continuous process. In the second stage, the oxidation is carried to completion in a batch process.

The air oxidation of aluminum alkyls is generally very rapid up to an oxidation level of about 90%. At this stage the oxidation rate becomes very slow and requires 2.5–4 hours of soak time with air to complete the oxidation. Catalysts such as titanium compounds are usually added during the last one-third of the oxidation to reduce by-product formation and improve yield. These titanium compounds further slow the oxidation rate which limits the amount that can be added without causing excessive reaction times.

We have now found that the oxidation rate can be increased by adding small amounts of a cobalt catalyst to the oxidation which effectively eliminates the need for a soak period.

In accordance with this invention there is provided a process for the oxidation of aluminum alkyls or partially oxidized aluminum alkyls, which process comprises reacting said aluminum alkyls or partially oxidized aluminum alkyls with oxygen or an oxygen containing material in the presence of a cobalt catalyst so as to convert said aluminum alkyls or partially oxidized aluminum alkyls to aluminum alkoxides.

Also provided is a process for preparing alcohols which comprises oxidizing aluminum alkyls or partially oxidized aluminum alkyls by reacting said aluminum alkyls or partially oxidized aluminum alkyls with oxygen or an oxygen containing material in the presence of a cobalt catalyst so as to convert said aluminum alkyls or partially oxidized aluminum alkyls to aluminum alkoxides and then hydrolyzing said aluminum alkoxides to form alcohols.

A preferred aluminum alkyl feed for the process of the invention comprises one or more compounds represented by the formula $R_3Al$, where R represents $C_2$ to about $C_{20}$ straight chain alkyl radicals, which can be the same or different. The feed can be prepared by the well known Ziegler chain growth process in which a $C_2-C_4$ alpha olefin, and usually ethylene, is reacted with an aluminum alkyl such as triethylaluminum to produce an aluminum alkyl product in which the chain length of the alkyl groups have a Poisson, or pseudo Poisson distribution.

The preferred chain lengths for linear primary alcohols useful, for example, in making detergents are from about $C_{10}$ to $C_{18}$ and especially $C_{12}$ to $C_{14}$. When the chain growth process is operated to produce aluminum alkyl products having such chain lengths, a larger than desired amount of the less useful $C_{20+}$ heavy ends is also produced. Therefore, it is more efficient to produce a lower average chain length aluminum alkyl feed, such as $C_8$ to $C_{12}$ and then to displace the lower alkyl groups using a molar excess of alpha-olefins having an average chain length of at least about 2 more carbons in order to form the heavier aluminum alkyl products from which the alcohols are prepared. For example, alpha-olefins having chain lengths of $C_{10}$ to about $C_{18}$. Such alpha-olefins can be obtained from the ethylene chain growth reaction on triethylaluminum, displacement of alkyl groups with lighter olefins, e.g. ethylene and/or butene, to provide a mixture of α-olefins, and then fractional distillation to separate out the desired longer chain alpha-olefins. Particularly, useful feeds for making alcohols for detergents are mixtures of $C_{10}$ to $C_{18}$ alpha-olefins having an average chain length of about $C_{12}$ to $C_{14}$. A single carbon number $C_{10}$ to $C_{18}$ alpha-olefin feed can also be used for displacement.

The first stage oxidation can be accomplished by continuously feeding the aluminum alkyls along with air or other molecular oxygen containing material to a reaction system such as series of heat exchangers. The oxidation is exothermic and the temperature is controlled in a range of from about 80° to 150° F. The reaction pressure is generally from about 20 to 60 psig. A stream of the partially oxidized feed can be recycled to the reactor to increase the degree of oxidation. The oxidation of the first two alkyl groups is rapid and a degree of oxidation of from about 50 to 65% is readily achieved without either significant formation of by-products, such as aldehydes, esters, olefins and paraffins, or the premature formation of free alcohols. In order to complete the oxidation without significant by-product formation, the partially oxidized material is first stripped to remove $C_{12}-C_{22}$ olefins, preferably diluted with an inert hydrocarbon solvent such as octane, and fed to the second oxidation stage along with a catalyst which acts to suppress the formation of by-products and aids in obtaining a high yield of aluminum alkoxide. Suitable by-product suppressing catalysts are known in the art and include compounds of Groups 3, 4, 5 and 12 metals of the new IUPAC notation for the Periodic Table. Preferred are titanium and zirconium halides. Most preferred is titanium tetrachloride. Other suitable catalysts are disclosed for example in U.S. Pat. No. 3,475,476, whose teachings are incorporated herein by reference. The catalysts are employed in amounts of metal in the catalyst of from about 100 to 5,000 ppm based on the total weight of aluminum compounds in the reaction mass. Although the catalyst helps to achieve a high yield of alkoxides by suppressing by-product formation, it also acts to retard the rate of oxidation in the second step.

In a typical second stage oxidation, the partially oxidized aluminum alkyls and a $TiCl_4$ catalyst are charged to a stirred batch reactor and air is fed to the reactor with the temperature being allowed to rise to about 175° F. The temperature is then controlled in a range, preferably of from about 100° to 200° F. When the oxygen content at the vent rises to about 7 to 8%, the soak period needed to complete the oxidation is started by co-feeding nitrogen to the reactor to maintain the oxygen content at the vent at about 7 to 8%.

The presence of a cobalt catalyst compound in the second stage oxidation in an amount, based on cobalt, of at least about 1 ppm, and preferably of from about 5 to 100 ppm, based on the total weight of the reaction mass, including the aluminum compounds and solvent, significantly increases the rate of oxidation without increasing by-product formation. This permits larger amounts of the by-product suppressing catalyst to be used without increasing cycle times and, in fact eliminates the present long soak times of 2½ to 4 hours which were previously needed in the second step of second stage oxidation. Therefore, the thruput and process capacity of existing equipment can be increased. The cobalt catalyst can be present during the first oxidation step and, in fact, we have found that residual catalyst from a prior displacement step will also increase the rate of oxidation.

Suitable cobalt catalysts include, but are not intended to be limited to cobalt acetylacetonate, and, preferably, cobalt carboxylates, i.e. cobalt naphthenate, cobalt acetate, cobalt tallate, cobalt (stearate), cobalt 2-ethyl-hexanoate, and the like. Amounts of catalyst of greater than 100 ppm can be used, but would add to the cost of the process and increase the amount of catalyst residue in the by-product aluminum salt.

The aluminum alkoxides can be hydrolyzed, as known in the art with water, steam, acid or base. Preferred are aqueous mineral acids such as HCl, $HNO_3$, $H_2SO_3$ and, most preferably, $H_2SO_4$.

The invention is further illustrated by, but is not intended to be limited to the following examples.

The oxidation apparatus consists of a one-liter Parr reactor and pump-around loop for cooling and gas/liquid separation. Air or nitrogen can be fed to the reactor through rotameters into a dip tube below the agitator. Aluminum alkyl is fed from a tank through a rotameter into the recirculation loop. In operation, a liquid/gas mixture is transferred from the reactor to a K.O. pot where the gas (nitrogen) is separated and vented to an oxygen analyzer. The liquid is then pumped through a cooler and rotameter and then back to the reactor. Liquid product is removed from the unit at the same rate as the feed.

In the first oxidation step, aluminum trialkyl is continuously fed and product removed from the system. In the second oxidation step, no aluminum trialkyl is fed or removed and the system operates in a batch mode. The operating procedure for each step is as follows:

First Oxidation

1. Fill feed tank with aluminum trialkyl/olefin mixture.
2. Pump about one liter of feed into the reactor and start gear pump to circulate liquid from the K.O. pot through the cooler and back to the autoclave.
3. Batch oxidize with air for 20–25 minutes to bring oxidation to 60–65 percent. Maintain reactor pressure at 40 psig.
4. Start aluminum alkyl feed at about 40 g/min and begin product withdrawal at same rate. Maintain temperature at 115°–150° F.

After about two liters of product has been collected, sample product and stop air and aluminum alkyl feed.

Second Oxidation

1. Vent the pressure off the reactor and add a weighed amount of $TiCl_4$ catalyst.
2. Pressure the reactor to 40 psig, start recirculation loop and heat to 120° F.
3. Begin air feed and slowly raise the temperature to 160° F.
4. When $O_2$ in the vent reaches 8%, begin soak period by cofeeding nitrogen to maintain 8% $O_2$ in the vent.
5. Continue soak period for 2 hours and then cool and remove product.

The product from second oxidation is fed to a Pope wiped-film still which removes the solvent and hydrocarbon impurities from the alkoxide with the bottoms temperature held at a minimum of 450° F. at 5 mm Hg vacuum.

The presence of 5 ppm cobalt as cobalt naphthenate in the second oxidation, which also contained 400 ppm of Ti as $TICl_4$, was observed to increase the oxidation rate at least 25%. Some increase in free alcohol was noted during alkoxide stripping. Upon acid hydrolysis, all of the cobalt was recovered with the alum as was the case with the following simulation. Washing and distillation of the crude alcohol product provided alcohol fractions which were within specifications. It is expected that free alcohol production during oxidation can be minimized by reducing or eliminating the soak period.

According to the hydrolysis process, the product alkoxide $Al(OR)_3$ from the wiped-film still is reacted in a circulation loop with sulfuric acid to produce crude alcohol and alum, $Al_2(SO_4)_3$. The product mixture is two-phase and the alum is separated from the mixture. The crude alcohol is then passed through an acid wash, a caustic wash and two water washes.

A normal alkoxide feed to which 20 ppm cobalt had been added in order to simulate the presence of residual catalyst was hydrolyzed. The cobalt did not change the process compared to cobalt-free hydrolysis and all of the added cobalt appeared in the alum.

Comparisons 1–3

Second Oxidation Procedure With No Cobalt Catalyst

1. Charge 9000 grams of partially oxidized (55–60%) aluminum alkyls from a first oxidation sample to the reactor system described above.

The alkyls are diluted with 20–30% of a suitable solvent such as octane.

2. Add 1.4 grams of $TiCl_4$ (388 ppm) and heat reactor contents to 135° F.
3. Start air feed at 2.2 SCFH and oxidize for 1.8 hours at which point the oxygen in the vent has reached 8 mole %. A sample taken at this stage in the reaction shows the % oxidation to be 92 mole %.
4. Reduce the air rate to 1.5 SCFH and co-feed 1.2 SCFH of $N_2$ to keep the vent oxygen at 8 mole % which is safely below the explosive range.
5. Gradually raise the temperature to 175° F. for the soak phase of the reaction.
6. After reacting for an additional 2,8 hours the oxidation is stopped. At this point the % oxidation is measured to be 99.4 mole %. The total yield of alkoxide was 94.1 mole %.

This procedure (Comparison 1) was repeated twice (Comparisons 2 and 3) with the reaction parameters and results shown in Table I.

Examples 1–3

Second Oxidation Procedure With Cobalt Catalyst Added

1. Charge 900 grams of the same feed as used in Comparison 1.
2. Add 1.47 grams TiCl₄ (408 ppm Ti) and 0.15 grams cobalt napthenate (10 ppm Co) and heat reactor to 125° F.
3. Start air feed at 3.3 SCFH and oxidize for 1.3 hours at which point the oxygen in the vent has reached 8 mole %.
4. The reaction is stopped and a sample of the product shows the % oxidation to be 99.7 mole %. Total yield of alkoxide was 95.0 mole %.

This procedure (Example 1) was repeated twice (Examples 2 and 3) with the reaction parameters and results shown in Table I.

TABLE I

SUMMARY OF OXIDATION RUNS

| Run No. | Temp. °F. Reac. | Temp. °F. Soak | ppm Ti | ppm Co | Time Hours Reac. | Time Hours Soak | % Oxidation Reac. | % Oxidation Soak |
|---|---|---|---|---|---|---|---|---|
| Comp. 1 | 135 | 170 | 388 | — | 1.8 | 2.8 | 92.0 | 99.4 |
| Comp. 2 | 135 | 175 | 446 | — | 1.3 | 1.8 | 91.5 | 97.8 |
| Comp. 3 | 134 | 175 | 416 | — | 1.8 | 2.7 | 93.2 | 99.9 |
| Ex. 1 | 125 | — | 408 | 10 | 1.3 | — | 99.7 | — |
| Ex. 2 | 125 | — | 416 | 10 | 1.5 | — | 99.9 | — |
| Ex. 3 | 126 | — | 435 | 10 | 1.2 | — | 99.1 | — |

The results shown in Table I demonstrate that the use of a cobalt catalyst increased the oxidation rate such that the soak period was not needed to achieve >99% oxidation.

What is claimed is:

1. A process for the oxidation of aluminum alkyls or partially oxidized aluminum alkyls, said process comprising, reacting said aluminum alkyls or partially oxidized aluminum alkyls with oxygen, air or other molecular oxygen containing gas mixture in the presence of a cobalt catalyst and a by-product suppressing catalyst selected from the group consisting of compounds of the Group 3, 4, 5 and 12 metals of the Periodic Table, so as to convert said aluminum alkyls or partially oxidized aluminum alkyls to aluminum alkoxides at an increased rate.

2. The process of claim 1 wherein said cobalt catalyst is present in the reaction mass in an amount to provide at least about 1 ppm of cobalt and said by-product suppressing catalyst is present in an amount to provide from about 100 to 5000 ppm of Group 3, 4, 5 or 12 metal based on the weight of aluminum compounds in the reaction mass.

3. The process of claim 2 wherein said by-product suppressing catalyst is TiCl₄ and said cobalt catalyst is a cobalt carboxylate.

4. The process of claim 2 wherein said cobalt catalyst is present in the reaction mass in amounts to provide from about 5 to 100 ppm of cobalt.

5. A process for the oxidation of aluminum alkyls, said process comprising the steps of:

A. partially oxidizing said aluminum alkyls by reacting said aluminum alkyls with gas mixture, air or other molecular oxygen containing material, and B. further oxidizing the partially oxidized aluminum alkyls from step A by reacting said partially oxidized aluminum alkyls with oxygen, air or other molecular oxygen containing gas mixture in the presence of a cobalt catalyst whereby at least about 90% by weight of the aluminum alkyls are oxidized to their corresponding aluminum alkoxides.

6. The process of claim 5 wherein said aluminum alkyls are from about 40 to 70 weight percent oxidized in step A.

7. The process of claim 6 wherein the step B oxidation is carried out in the presence of a by-product suppressing catalyst selected from the group consisting of compounds of the Group 3, 4, 5 and 12 metals of the Periodic Table.

8. The process of claim 7 wherein said cobalt catalyst is present in the reaction mass in an amount to provide at least about 1 ppm of cobalt and said by-product suppressing catalyst is present in an amount to provide from about 100 to 5000 ppm of Group 3, 4, 5 or 12 metal based on the weight of aluminum compounds in the reaction mass.

9. The process of claim 8 wherein said by-product suppressing catalyst is TiCl₄ and said cobalt catalyst is a cobalt carboxylate.

10. The process of claim 8 wherein said cobalt catalyst is present in the reaction mass in amounts to provide from about 5 to 100 ppm of cobalt.

11. A process for the information of alcohols by the oxidation and hydrolysis of aluminum alkyls said process comprising the steps of:

A. partially oxidizing said aluminum alkyls by reacting said aluminum alkyls with oxygen, air or other molecular oxygen containing gas mixture, B. further oxidizing the partially oxidized aluminum alkyls from step A by reacting said partially oxidized aluminum alkyls with oxygen, air or other molecular oxygen containing gas mixture in the presence of a cobalt catalyst whereby at least about 90% by weight of the aluminum alkyls are oxidized to their corresponding aluminum alkoxides, and C. hydrolyzing said aluminum alkoxides to form said alcohols.

12. The process of claim 11 wherein said aluminum alkyls are from about 40 to 70 weight percent oxidized in step A.

13. The process of claim 12 wherein the step B oxidation is carried out in the presence of a by-product suppressing catalyst selected from the group consisting of compounds of the Group 3, 4, 5 and 12 metals of the Periodic Table.

14. The process of claim 13 wherein said cobalt catalyst is present in the reaction mass in an amount to provide at least about 1 ppm of cobalt and said by-product suppressing catalyst is present in an amount to provide from about 100 to 5000 ppm of Group 3, 4, 5 or 12 metal based on the weight of aluminum compounds in the reaction mixture.

15. The process of claim 14 wherein said by-product suppressing catalyst is TiCl₄ and said cobalt catalyst is a cobalt carboxylate.

16. The process of claim 14 wherein said cobalt catalyst is present in the reaction mass in amounts to provide from about 5 to 100 ppm of cobalt.

* * * * *

UNITED STATES PATENT AND TRADEMARK OFFICE
CERTIFICATE OF CORRECTION

PATENT NO. : 5,430,165
DATED : July 4, 1995
INVENTOR(S) : WILLIAM L. COX, ET AL.

It is certified that error appears in the above-identified patent and that said Letters Patent is hereby corrected as shown below:

Column 6:
Claim 5, lines 2 and 3 read: "...with gas mixture, air or other molecular oxygen containing material,...", but should read: -- ...with oxygen-, air or other molecular oxygen containing gas mixture,... --

Claim 11, line 32 reads: "... for the information...", but should read: -- ...for the formation... --.

Signed and Sealed this

Sixteenth Day of January, 1996

Attest:

BRUCE LEHMAN

*Attesting Officer*     *Commissioner of Patents and Trademarks*